(12) United States Patent
Potts et al.

(10) Patent No.: US 8,236,486 B2
(45) Date of Patent: Aug. 7, 2012

(54) FLUSH PRESERVATION SOLUTION

(75) Inventors: David Potts, Leeds (GB); Jeremy Peter Alan Lodge, Leeds (GB)

(73) Assignee: The Leeds Teaching Hospital NHS Trust, Leeds (GB)

( * ) Notice: Subject to any disclaimer, the term of this patent is extended or adjusted under 35 U.S.C. 154(b) by 595 days.

(21) Appl. No.: 12/379,515

(22) Filed: Feb. 24, 2009

(65) Prior Publication Data

US 2009/0226877 A1  Sep. 10, 2009

Related U.S. Application Data

(62) Division of application No. 10/415,355, filed as application No. PCT/GB01/05102 on Nov. 20, 2001, now Pat. No. 7,510,823.

(30) Foreign Application Priority Data

Nov. 22, 2000  (GB) .................................. 0028414.1

(51) Int. Cl.
*A01N 1/00* (2006.01)
*A01N 1/02* (2006.01)

(52) U.S. Cl. ........................................ 435/1.1; 435/1.2

(58) Field of Classification Search .................. None
See application file for complete search history.

(56) References Cited

U.S. PATENT DOCUMENTS

| | | | |
|---|---|---|---|
| 4,879,283 A | 11/1989 | Belzer et al. | |
| 4,920,044 A | 4/1990 | Bretan, Jr. | |
| 4,938,961 A | 7/1990 | Collins et al. | |
| 5,145,771 A | 9/1992 | Lemasters et al. | |
| 5,162,374 A | 11/1992 | Mulieri et al. | 514/640 |
| 5,370,989 A | 12/1994 | Stern et al. | |
| 5,405,742 A | 4/1995 | Taylor | |
| 5,484,789 A | 1/1996 | Thurman et al. | |
| 6,080,730 A | 6/2000 | Lemasters et al. | |
| 6,140,123 A | 10/2000 | Demetriou et al. | |
| 7,510,823 B2 * | 3/2009 | Potts et al. | 435/1.1 |

FOREIGN PATENT DOCUMENTS

| | | |
|---|---|---|
| CN | 1178070 | 4/1998 |
| EP | 0407780 | 1/1991 |
| EP | 0806140 | 11/1997 |
| EP | 0562188 | 9/1998 |
| EP | 1000541 | 5/2000 |
| FR | 2723818 | 3/1996 |
| GB | 2249937 | 5/1992 |
| GB | 2270614 | 3/1994 |
| WO | 9106293 | 5/1991 |
| WO | 9114364 | 10/1991 |
| WO | 9304578 | 3/1993 |
| WO | 9505076 | 2/1995 |
| WO | 9835551 | 8/1998 |
| WO | 9915011 | 4/1999 |
| WO | 0027189 | 5/2000 |
| WO | 0030442 | 6/2000 |
| WO | 0152647 | 7/2001 |
| WO | 0154495 | 8/2001 |

OTHER PUBLICATIONS

Buyukgebiz et al., "The effects of thromboxane sythase inhibition on reperfusion injury and endothelin-1,2 levels in allograft kidney transplantation in rats", Research in Experimental Medicine 198: 289-298 (1999).*
Lindsay et al., "Dazoxiben, UK 38,485 and aspirin: duration of effect for preventing thrombotic sudden death in rabbits", Thrombosis Research 43: 177-186 (1986).*
F.O. Belzer, "Evaluation of Preservation of the Intra-Abdominal Organs", Transplantation Proceedings, Vo. 25, No. 4 (Aug. 1993), pp.2527-2530.
Roger Bell et al., "A Comparison of Flushing Solutions for Liver Procurement Using an Isolated Perfused Porcine Model", Aust. N.Z. J. Surg. (1994) 64, 565-568.
G.M. Collins, "What Solutions Are Best? Overview of Flush Solutions", Transplantation Proceedings, 29, 3543-3544 (1997).
T. A. Churchill et al., "Investigation of a Primary Requirement of Organ Preservation Solutions", Transplantation, vol. 65, 551-559, No. 4, Feb. 27, 1998.
F. Mühlbacher, et al., "Preservation Solutions for Transplantation", Transplantation Proceedings, 31, 2069-2070 (1999).
K. K. Changani et al. "Improved Preservation Solutions for Organ Storage", Transplantation, Vo. 68, 345-355, No. 3, Aug. 15, 1999.
Alessandro, et al. "Organ Preservation", Horizons in Organ Transplantation, vol. 7, No. 5, pp. 1083-1093, Oct. 1994.
Collins et al., "New Organ Preservation Solutions", Kidney International, vol. 42, Suppl. 38, pp. S-197-S-202, 1992.
Andrews, et al., "Factors That Improve the Preservation of Nephron Morphology During Cold Storage", Laboratory Investigation, vol. 46, No. 1, pp. 100-120, 1982.
Belzer, et al., "24-Hour and 72-Hour Preservation of Canine Kidneys", The Lancet, pp. 536-539, Sep. 9, 1967.
Belzer, et al., "Principles of Solid-Organ Preservation by Cold Storage[1]", Transplantation, vol. 45, No. 4, pp. 673-676, Apr. 1988.
Coffey, et al., "Ultrastructure of Kidney Preservation: Varying the Amount of an Effective Osmotic Agent in Isotonic and Hypertonic Preservation Solutions", Transplantation, vol. 35, No. 2, pp. 136-142, 1983.

(Continued)

*Primary Examiner* — Sandra Saucier
(74) *Attorney, Agent, or Firm* — Jacobson Holman PLLC

(57) ABSTRACT

Flush preservation solution for the preservation of cells in the absence of a blood supply comprising:
v) water for injection; and
vi) at least one saccharide such as a monosaccharide, disaccharide, trisaccharide, or polysaccharide and
vii) at least one component with pH buffer properties; and
viii) at least one component with calcium transport blocking properties or an anti-calcium action activity;
method for the preparation thereof; use thereof in transplantation including organs from heart beating or non heart beating donors, in surgery including any situation of warm or cold ischaemia, cardioplegia or open heart surgery, whole limb or whole body preservation in experimentation on living tissues or in culturing and preserving engineered cells, tissues and organs, limbs or the whole body; method for flushing, preserving or flush preservation of cells; and a kit of parts comprising the solution components.

2 Claims, 7 Drawing Sheets

OTHER PUBLICATIONS

Collins, et al., "Kidney Preservation for Transplantation 1. Twelve-Hour Storage in Rabbits", Transplantation Proceedings, vol. I, No. 3, pp. 801-807, Sep. 1969.

Ferwana, et al., "Unilateral Renal Ischaemia in the Rat: Effect of Contralateral Nephrectomy and Intrarenal Flush with Phosphate-Buffered Sucrose", Clinical Science, vol. 74, pp. 261-268, 1988.

Ferwana, et al., "Effect of Phosphate-Buffered Sucrose Flush Solution Upon the Initial Phase of Ischaemic Acute Renal Failure in the Rat", Clinical Science, vol. 77, pp. 77-84, 1989.

Isemer, et al., "Kidney Procurement With the HTK Solution of Bretschneider", Transplantation Proceedings, vol. XX, No. 5, pp. 885-886, Oct. 1988.

Lam, et al., "Improved 72-Hour Renal Preservation With Phosphate-Buffered Sucrose", Transplantation, vol. 47, No. 5, pp. 767-771, May 1989.

Ross, et al., "72-HR Canine Kidney Preservation Without Continuous Perfusion[1]", Transplantation, vol. 21, No. 6, pp. 498-501, 1976.

Collins, et al., "Kidney Preservation for Transportation Initial Perfusion and 30 Hours' Ice Storage", The Lancet, pp. 1219-1222, Dec. 6, 1969.

Pirie, et al., "A Comparison of the Relative Effectiveness of Three Transplant Preservation Fluids Upon the Integrity and Function of Rabbit Proximal Convoluted Tubules Perfused in vitro", Clinical Science, vol. 70, pp. 443-452, 1986.

Belzer, "Evaluation of Preservation of the Intra-Abdominal Organs", Transplantation Proceedings, vol. 25, No. 4, pp. 2527-2530, Aug. 1993.

Bell, et al., "A Comparison of Flushing Solutions for Liver Procurement Using an Isolated Perfused Porcine Model", Aust. N.Z. J. Surg., vol. 64, pp. 565-568, 1994.

Collins, "What Solutions Are Best? Overview of Flush Solutions", Transplantation Proceedings, vol. 29, pp. 3543-3544, 1997.

Churchill, et al., "Investigation of a Primary Requirement of Organ Preservation Solutions", Transplantation, vol. 65, No. 4, pp. 551-559, Feb. 27, 1998.

Mühlbacher, et al., "Preservation Solutions for Transplantation", Transplantation Proceedings, vol. 31, pp. 2069-2070, 1999.

Changani, et al., "Improved Preservation Solutions for Organ Storage", Transplantation, vol. 68, No. 3, pp. 345-355, Aug. 15, 1999.

Keraly et al., "Conditions affecting the responses of human platelets to epinephrine", Thrombosis and Haemostasis 60 (2) : 209-216 (1988).

Indge, "The isolation and properties of the yeast cell vacuole", J. General Microbiology 51 (3): 441-6 (1968).

Fischer et al., "Long term survival of liver transplantation in rats following 18 hour hypothermic ischemic storage", Chirurgisches Forum fuer Experimentelle und klinische Forschung (1982), 1-6.

Sigma-Aldrich Catalog, pp. 1-11, accessed Feb. 12, 2008, http://www.sigmaaldrich.com/Area_of_Interest/Biochemicals/BioUltra/Biological_Buffers.html.

English translation of CN 1178070, translated in Apr. 2007, pp. 1-63.

* cited by examiner

Reperfusion Circuit: liver

Perfusion circuit for the heart

Bile flow rate [ul. (g liver)$^{-1}$. (2h)$^{-1}$] during the reperfusion for the SOL 4, UW and SOL 20 groups following 24 hour cold preservation

*$P<0.05$ (vs SOL 20)

Bile acid concentration (umol/L) in bile during the reperfusion for the SOL 4, UW and SOL 20 groups following 24 hour cold preservation Bile acid extractions (%) during the reperfusion for the SOL4, UW and SOL 20 groups following 24-hour cold preservation

*P<0.05 (vs SOL 20)

Oxygen consumption [umol. (g liver)$^{-1}$, (min$^{-1}$)] during the reperfusion for the SOL4, UW and SOL 20 groups following 24-hour cold preservation

*P<0.05 (SOL 4 vs UW and SOL 4, UW vs SOL 20))

Liver weight change (%) after 24-hour cold preservation and after 2-hour reperfusion for the UW and PBSL groups Bile Flow in consecutive 15 min periods for PBSL and UW groups following 24 hour cold preservation AST release during reperfusion for the PBSL and UW groups following 24 hour cold preservation ALT release during reperfusion for the PBSL and UW groups following 24 hour cold preservation

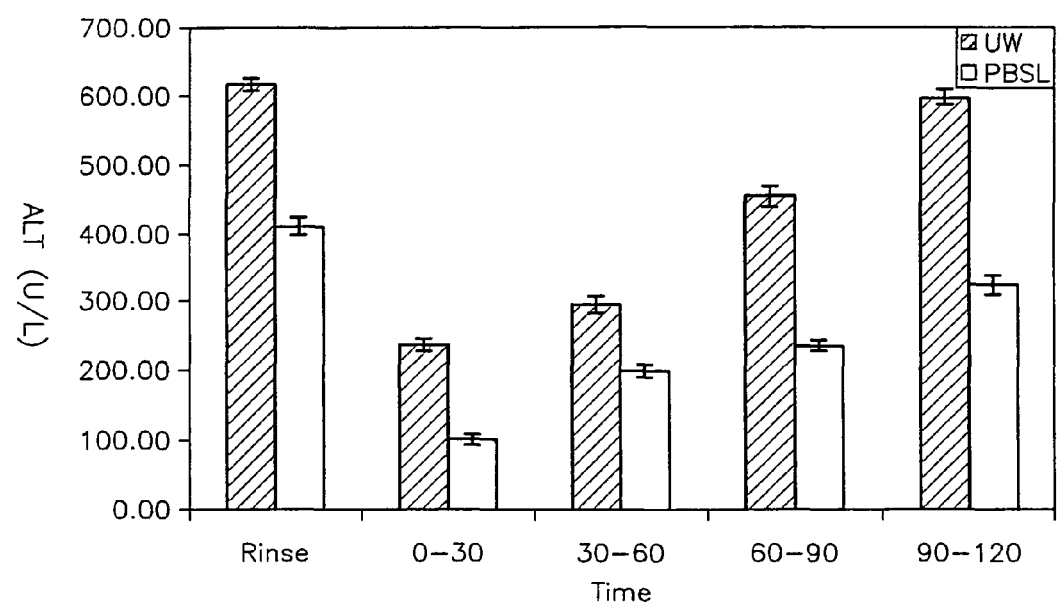

FLUSH PRESERVATION SOLUTION

This is a Divisional of U.S. patent application Ser. No. 10/415,355, filed Aug. 5, 2003, which issued as U.S. Pat. No. 7,510,823 on Mar. 31, 2009, which is a nationalization of PCT/GB01/05102 filed Nov. 20, 2001, which claimed priority of Great Britain application No. 0028414.1 filed Nov. 22, 2000, the subject matter of which is incorporated by reference herein

BACKGROUND OF THE INVENTION

The present invention relates to a flush preservation solution to keep cells without a blood supply alive, the use thereof to prevent damage to cells in transplantation, surgery, experimentally and in vitro, a method for preservation, flush or flush preservation, a method for treatment and a kit of parts comprising the solution.

Organ transplantation is now available for kidney, liver, heart, lung, pancreas and intestine. At retrieval a transplant organ is flushed through its vasculature with a preservation solution. This solution is designed to facilitate the reduction of temperature of the organ, prevent cell swelling, remove oxygen free radicals, control pH, reduce ischaemic damage, extend the safe time for which organs can be kept out of the body and facilitate recovery of the organ upon reperfusion.

Important flush solutions were introduced by Belzer in 1967 and Collins in 1969, subsequently modified to Euro-Collins (EC), Marshall (1976), Bretschneider (see Isemer et al 1988), and others. University of Wisconsin solution (UW), the most successful of all solutions, was introduced in 1988 by Belzer and his colleagues. There remains a need for improved flush preservation. Recent evidence indicates that a high quality graft provides both better immediate function and a longer functional graft lifetime.

This area of the literature has been reviewed by: Belzer, 1993; Belzer & Southard, 1988; Bonventre and Weinburg, 1992; Changani et al, 1999; Churchill & Kneteman, 1998; Collins, 1997; Collins & Wicomb, 1992; D'Allesandro et al, 1994; Muhlbacker et al, 1999 and Southard & Belzer, 1995.

A simple flush solution containing only sodium phosphate and sucrose was shown by Andrews and Coffey in 1982, and by Coffey and Andrews in 1983 to protect the morphology of kidney tubules from ischaemic damage. We carried out functional tests and found a similar solution (PBS140) to be highly successful in the preservation of kidney tubules as judged by microperfusion (Pirie and Potts, 1986) when compared to established preservation solutions (EC and Collins C2 solutions). PBS140 was found to provide better preservation of morphology and function of proximal tubules than other solutions. PBS140 was also found to be effective in the preservation of whole kidney function by Ferwana, Pirie and Potts in 1988 and 1989. In experimental transplantation Lam, Mayor, Potts and Giles (1989) found PBS140 to provide highly effective preservation which compared favourably with Hyperosmolar Citrate and UW solution (Lodge, Perry, Skinner, Potts and Giles 1991). PBS140 was tested clinically at Leeds and found to work well for human kidney transplantation (Ahmad, Kashi, Helmy, Hadingham, Potts and Lodge, 1997).

U.S. Pat. No. 4,920,044 describes flush and storage solutions which contain buffers, 20-37 grams per liter mannitol and 0-1.0 grams per liter verapamil. The solutions also contain magnesium and calcium ions, allopurinol and adenosine. The solutions have pH of 7.20-7.50 and osmolality of 255-425 osm/kg. The solutions are used eg. in the transplantation of organs such as kidneys, as flush solutions and further as storage solutions. Examples are shown of 50 hour cold storage with investigation of animal survival, insulin clearance, renal HPLC biopsy, serum creotins and the like in post storage kidney transplants.

U.S. Pat. No. 5,145,771 describes rinse or preservation solutions for organs and tissues for transplant, containing fructose and glucose, nicardipene (calcium blocker), buffer, solutes, allopurinol, glutathione and modified hydroxyethyl starch (colloid). Experiments show 12 hour cold storage of livers with investigation of liver damage (SGOT activity, clotting time, haem, and oxygen fraction) post transplant.

U.S. Pat. No. 5,405,742 describes blood substitute solutions for purging or maintenance of organs during surgery, or for preserving organs for transplantation. The solutions contain solutes, mannitol, buffers, glutathione, an impermeant anion which is lactobionate, iron-chelating agents, calcium channel blockers such as nicardipine and allopurinol. Experiments show three hours cold heart bypass circulation with investigation of serum levels post bypass.

U.S. Pat. No. 5,370,989 describes solutions for organ preservation or maintenance which contain a vasodilator, and also D-glucose, buffers, inorganic ions, and preferably other components such as a calcium blocker, colloids, adenosine etc. Experiments show 24 hours heart preservation with investigation of preservation rating (0-5).

CN-A-1176738 describes solutions for preserving organs for transplantation which contain sugar, a potassium phosphate buffer, the calcium channel blocker verapamil, lactobionate, solutes, a colloid (dextran), allopurinol and reduced glutathione and adenosine.

With the advent of improved immunosuppression came the need for a high performance multi-organ flush solution.

Numerous workers have investigated the development of improved solutions, and in particular of simpler solutions incorporating a number of additives. Efforts have been made to rationalise the results obtained with different formulations. Nevertheless it is apparent that apparently interchangeable additive types may in fact have different effects from those anticipated, this makes formulations extremely specific both in terms of a given type of additive, and in terms of other components present with a given additive since the function is dependent on the formulation as a whole and not simply on an individual constituent. It is moreover apparent that a universal flush solution is a misleading objective, since different organs have quite widely differing requirements. Individual workers have however attempted to focus on essential components which form the basis for flush solutions which may be adapted for specific organs. A number of reviews of the subject are of relevance, in particular "Evaluation of preservation of the intra abdominal organs, F O Belzer, Transplantation Proceedings, vol 25, No 4 (August) 1993, P2527-2530, "Organ Preservation" D'Alessandro et al, Horizons in Organ Transplantation, Vol 74, No. 5, 1994 page 1083-1093, "A comparison of Flushing Solutions for Liver procurement using an isolated perfused Porcine Model", Bell et al, Aust. N. Z. J. Surg. (1994) 64, 565-568, "New Organ Preservation Solutions", Collins et al, Kidney International, vol 42, Suppl. 38 (1992) PS197-S202, "Improved Preservation Solutions for Organ Storage", Changani et al, Transplantation, vol. 68, 345-355, No. 3, 1999 and "Investigation of a Primary Requirement of Organ Preservation Solutions", Churchill et al, Transplantation, vol. 65, 551-559, No. 4, 1998. Although in part instructive, the individual work and the reviews present so many variables that any meaningful deductions cannot as such be drawn. Design concepts are proposed, such as designing a formulation around essential cellular constituents which are lost or broken down during preservation, and a contrasting concept of designing formulations around constituents which interact with the natural cellular functions and constituents to prevent breakdown, maintain certain functioning or arrest other functioning and the like. The result is that any effective flush solution is likely to be derived by diligent experiment, rather than by deduction or analysis from existing work.

Accordingly there remains a need for a commercially viable and effective flush solution which enables extended preservation of cells in particular of organs and living tissues, including engineered organs and tissues, which provides improved versatility, effectiveness and reperfusion in transplantation, in surgery, including any situation of warm or cold ischaemia, cardioplegia and open heart surgery, whole limb, whole body, or in experimentation.

SUMMARY OF THE INVENTION

We have carried out experiments to develop an improved solution for liver transplantation. It emerged that sucrose-phosphate buffer solution provided good basic preservation. The incorporation of a number of additives produced a solution that provided better preservation than UW solution as judged by greater bile flow, bile acid extraction, and reduced liver weight gain and release of liver enzymes. This approach provided a new flush solution for use on kidney and liver.

The heart has different requirements. The new solutions developed for kidney and liver were not found to be suitable for heart. However, a basic sucrose-phosphate buffer solution, with some modifications was found to be effective in the preservation of heart tissue. These different requirements are almost certainly related to the muscular structure of the heart.

Accordingly in the broadest aspect of the invention there is provided a flush preservation solution for the preservation of cells in the absence of a blood supply comprising:
i) water for injection; and
ii) at least one saccharide such as a monosaccharide, disaccharide, trisaccharide, or polysaccharide and
iii) at least one component with pH buffer properties; and
iv) at least one component with calcium transport blocking properties or an anti-calcium action activity.

The flush solution may consist only of these components, in which case it is suited for preservation of universal cell types and functioning, in particular for preservation of simple cell systems, alternatively it may be provided together with one or more further substituents specifically suited to the preservation of a desired type or function of cell, in particular in the preservation of complex cell systems such as organs or living tissue, more particularly for small or large animals, most particularly human organs and living tissue.

By means of the present invention we have surprisingly found that a highly effective universal basic solution may be supplemented to equal effect with a number of different constituents for different application. This has a number of advantages in terms of improving existing solutions, with reduced damage during preservation and the possibility to extend preservation periods, in addition to the provision of a formulation kit from which to create a particular desired formulation, with the associated convenience and cost implications which will render such formulation commercially viable.

The prior art has attempted to teach the basis for a universal preservation solution, however, teaching is widely divergent, and even the identification of a combination of saccharide and pH buffer is not universally accepted. The present invention has found the hereinbefore defined flush preservation solution to be universally acceptable, based on experiments and without attempting to rationalise the underlying preservation mechanism.

All components of the flush preservation solution of the invention satisfy National or International Pharmacopoeial Standards of purity where applicable. Water for injection is typically purified and de-ionized prior to sterilization.

A saccharide is selected from sucrose, raffinose, mannitol, and is preferably sucrose.

A pH buffer is selected from a sodium phosphate buffer, a potassium phosphate buffer and the like, preferably $Na_2HPO_4$ $NaH_2PO_4$, $K_2HPO_4$, $KH_2PO_4$ and the like.

A calcium transport blocker or anti-calcium activity agent is selected from any known calcium transport or channel blocker such as nicardipine, diltiazem, verapamil, nisoldipine, chlorpromazine or trifluorperazine, preferably nicardipine and/or diltiazem.

Without being limited to this theory, reference is made hereinbelow to components by function based on commonly accepted physiological activity, however for the avoidance of doubt, components listed may contribute additional or different function to that attributed, and this should not be seen as a limitation thereof. Additionally functional equivalents to those listed may be considered within the scope of this invention.

Preferably the flush preservation solution comprises one or more additional components selected from:
v) at least one anion that is largely impermeable into cells, preferably is an impermeant sequestering anion;
vi) a thromboxane inhibitor; and
vii) at least one component with colloid osmotic properties.

An impermeant sequestering anion preferably comprises lactobionate or lactobionic acid.

A thromboxane inhibitor prevents blood clotting and preferably comprises aspirin.

A colloidal osmotic preferably comprises polyethylene glycol (peg), succinylated gelatin (as in Gelofusine), Ficoll (a polysaccharide) or a starch product.

Alternatively or additionally, the flush preservation solution of the invention may comprise one or more components selected from:
viii) inorganic or organic solutes;
ix) a component or components with calcium chelating properties; and
x) a component or components with iron chelating properties.

Preferably an inorganic or organic solute comprises an inorganic solute and is an electrolyte including cations and/or anions, for example selected from $Na^+$, $K^+$, $Cl^-$, $OH^-$, $Ca^{2+}$, $Mg^{2+}$ and the like.

Preferably a calcium chelater comprises citrate or EGTA and an iron chelater comprises EDTA.

Alternatively or additionally the flush preservation solution of the invention may comprise one or more components selected from:
xi) one or more amino acids
xii) at least one component that is effective against oxygen free radicals or the production of oxygen free radicals;
xiii) and at least one component of the energy supply system or which influences the energy supply system or a ketone body.

Preferably an amino acid is glutamine, glycine or n-acetyl-cysteine.

Preferably oxygen free radical inhibitors are selected from allopurinol and reduced glutathione, more preferably a combination thereof.

Preferably an energy supply system component comprises adenosine. Preferably a ketone body comprises beta-hydroxy butyrate.

Alternatively or additionally the flush preservation solution of the invention may comprise additional components for a specific function selected from:

xiv) at least one component that acts reversibly upon cross-bridge function in muscle, preferably butane-dione-monoxime;
xv) at least one component that influences the insertion and removal of proteins into and from cell membranes, preferably Taxol;
xvi) at least one component of the intracellular signal transduction system or which modifies this system, preferably a protein kinase inhibitor or a calmodulin inhibitor,
xvii) at least one component that has a membrane stabilising action, preferably ranolazine, and the like.

The flush preservation solution of the invention is preferably formulated to comply with a desired range of the pharmacopoeially acceptable physical properties. Preferably the solution has a pH in the range 6.5-7.8, more preferably 6.5-7.0, most preferably 6.8-7.0.

Preferably the solution has osmolality in the range 300-450 mosmol/l, more preferably 350-400 mosmol/l.

In a further aspect of the invention there is provided a process for the preparation of a flush preservation solution as hereinbefore defined. The solutions are suitably made up by methods as known in the art by simple admixture under pharmacopoeially acceptable conditions. Preferably components are determined and incorporated in a desired molar concentration.

It will be appreciated that variation may be specific or non-specific to the effectiveness of the solution and that an amount of variation which has no effect on the performance of the fluid is considered within the scope of this invention. Selection of component type, requiring an amount of verification by routine experimentation, is considered within the scope of this invention.

BRIEF DESCRIPTION OF THE DRAWINGS

FIG. 10: A chart comparing LDH release after 24 hours of cold preservation using UW or PBSL solution.

DETAILED DESCRIPTION AND PREFERRED EMBODIMENTS

Figure 1A:
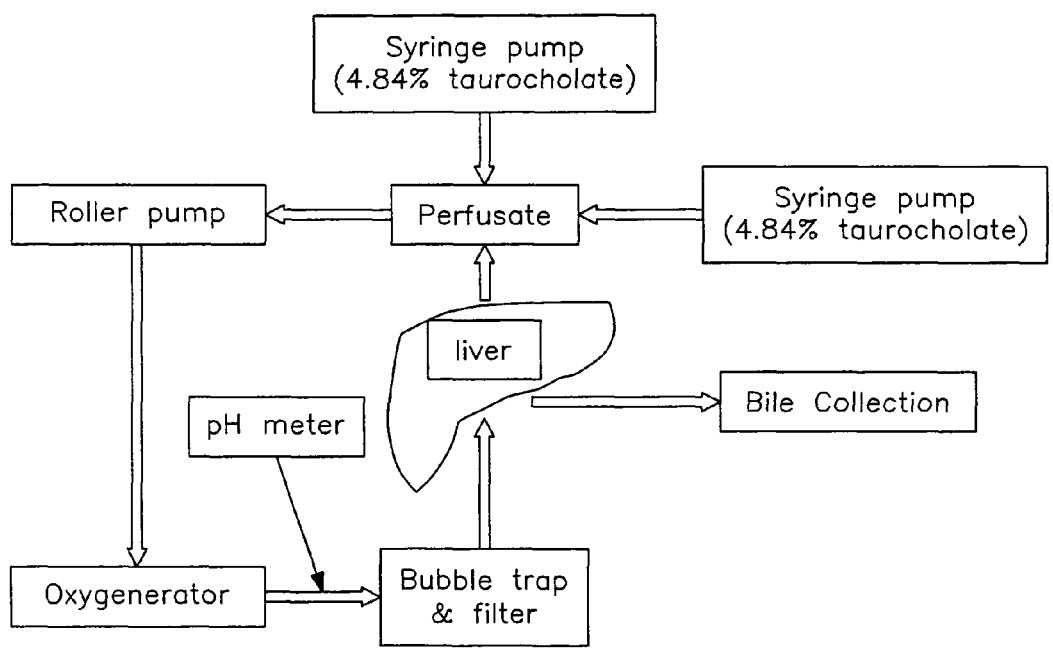
FIG. 1a: A schematic diagram of the liver reperfusion apparatus is shown.

Preferably a component (ii) is present in an amount in the range 50-150 mmol/l, for example approximately 100 mmol/l; each component (iii), (v), (viii) is present in a total amount in the range 15-75 mmol/l, for example approximately 15-20 or 40-70 mmol/l; component (xi) is present in an amount in the range 15-30 mmol/l, for example approximately 20 mmol/l; component (xii) is present in a total amount in the range up to 5 mmol/l, for example approximately 3-5 mmol/l; component xiii (ketone body component) is present in an amount in the range of up to 40 mmol/l, for example 25 mmol/l; component (vii) is present in an amount in the range 0.5-3.0 mmol/l, for example approximately 0.75-1.33 mmol/l, such as 1.0 mmol/l, and 20,000 mw; component (vi) is present in an amount in the range 0.3-1.0 mmol/l, for example 0.5 mmol/l; component (iv) is present in an amount in the range 0.0005-0.1 mmol/l, for example approximately 0.0005-0.5 mmol/l.

Other components will typically be present in minor amounts for example in the range up to 1 mmol/l.

In the case of certain components present as 2 or more types, the relative amounts may be critical or non-critical. Preference xii) is for approximately 3 mmol/l reduced glutathione and 0.35 to 0.4, more preferably 0.4 mmol/l allopurinol.

Preference viii) is for electrolytes as follows:
$Na^+$ 50-150 mmol/l
$K^+$ 0-25 mmol/l
$CL^-$ 0-100 mmol/l
$OH^-$ 0-75 mmol/l
$Ca^{2+}$ 0-2 mmol/l
$Mg^{2+}$ 0-10 mmol/l Preferably a solution according to the invention is prepared and stored under anoxic condition in the absence of UV light. It is a particular advantage that the solution as defined comprising components (i)-(iv) may be stored for extended periods, and additional components added immediately prior to use The flush preservation solution of the invention as hereinbefore defined preferably comprises the basis components (i)-(iv) together with additional components for specific function. The solution for use in preserving organs is particularly of greater complexity than that for preserving simple cell systems, however we have found that the solution may nevertheless be relatively straightforward.

Preferably a flush preservation solution for intra abdominal organs such as kidney, liver, pancreas, intestine, bowel and the like comprises components (i)-(iv) as hereinbefore defined together with at least one component selected from (v), (vi) and (vii), and more preferably additionally (viii), (xi), (xii) and (xiii).

Preferably an organ used to preserve muscular organs such as the heart comprises components (i)-(iv) as hereinbefore defined together with components selected from (viii), and more preferably additionally at least one component (xiv) as hereinbefore defined.

Preferably a flush preservation solution for liver, kidney and pancreas preservation comprises a combination of component classes given below, more preferably of the specific type listed, most preferably substantially in the amount listed:

| Component | Type | Amount mmol/L |
| --- | --- | --- |
| v) | Lactobionic acid | 50 |
| viii) | KOH | 15 |
| viii) | NaOH | 35 |
| xii) | Glutathione | 3 |
| iii) | Na$_2$HPO$_4$ | 26.45 |
| iii) | NaH$_2$PO$_4$ | 16.66 |
| xi) | Glutamine | 20 |
| ii) | Sucrose | 100 |
| vi) | Aspirin | 0.5 |
| xii) | Allopurinol | 0.4 |
| iv) | Nicardipine | 0.005 |
| vii) | Peg (20,000 MW) | 1 |

Preferably a flush preservation solution for heart preservation comprises a combination of component classes given below, more preferably of the specific type listed, most preferably substantially in the amount listed:

| Component | Type | Amount mmol/L: |
| --- | --- | --- |
| iii) | Na$_2$HPO$_4$ | 42.3 |
| iii) | NaH$_2$PO$_4$•2H$_2$0 | 10.67 |
| iii) | KH$_2$PO$_4$ | 16 |
| ii) | Sucrose | 100 |
| viii) | MgCl$_2$ | 5 |
| viii) | CaCl$_2$ | 0.6 |
| viii) | NaCl | 12 |
| iv) | Diltiazem | 0.5 |

We have moreover surprisingly found that the effectiveness of constituents of a flush preservation solution according to the invention is effected by the presence of other constituents. Without being limited to this theory it seems that the effect of certain constituents is either negated or simply not transmitted to a target site, in the absence of constituents ensuring the maintenance of other cell functions. For example it is believed that the presence of an impermeant sequestering anion (v) and the presence of a colloid osmotic agent (vii) is more effective in combination than alternative, and the presence of both allopurinol and reduced glutathione as oxygen free radical quench (xii) is more effective than the individual compounds. We have found that this is particularly useful in selecting specific solutions for preservation of specific cell, tissue or organ types, whereby certain combinations are useful for one type and may simply be substituted by those combinations suited for another type. As hereinbefore described, the substitution may be related to the presence of a substituent in the normally functioning cells or may interact with cell functioning in some manner. In a preferred embodiment of the invention we found that the impermeant sequestering anion (v) together with the colloid osmotic agent (vii) are suited for preservation of intra abdominal organs, and are substituted by a muscle cross bridge function agent (xiv) in tailoring a fluid for use in preservation of muscular organs such as the heart.

Accordingly the finding according to the present invention is that certain substituents are essential for the preservation of the principle cell functions essential to all cell types and these have been identified as the component (i)-(iv) as hereinbefore defined. Whilst this formulation may be highly effective or satisfactory in preserving simple tissue or cellular systems, if it is desired to preserve organs or cell systems requiring or providing unusual or more complex cell function it is necessary to incorporate substituents specifically directed to preserve the requisite or provided function, whether this be muscular, electrical, specific membrane activity, energy supply and the like.

In a further aspect of the invention there is provided a method for the preparation of a flush preservation solution comprising adding components in sequence to water, with the exception of component vii) and unstable components if any, and dissolving, adding component vii) if any and making the solution nearly up to volume and finally making up to volume to regulate pH, sterilising and cooling. The solution may be stored if desired with subsequent addition of any unstable components immediately prior to use.

In a further aspect of the invention there is provided the use of a flush preservation solution as hereinbefore defined as a flush solution, preservation solution or flush preservation solution for the preservation of cells in the absence of a blood supply, in particular to prevent damage to organs, living tissues and cells. The solution is suited for use with small or large animal or mammalian, in particular human organs, living tissues and cells.

The use of the solution may be in transplantation including organs from heart beating or non heart beating donors, in surgery including any situation of warm or cold ischaemia, cardioplegia or open heart surgery, whole limb or whole body preservation, in experimentation on living tissues, in culturing and preserving engineered cells, tissues and organs and the like. Preferably the solution is used as a flush solution brought into contact with cells, living tissues, organs, limbs or the whole body via the vascular system, and optionally additionally serves as a preservation solution for storage of flushed cells, tissues and organs. In an embodiment of the invention a first solution as hereinbefore defined is used to flush the cells, tissue, organ, limb or body and a second solution is used for the preservation thereof, or part thereof. For example the flush solution comprises components (i)-(iv) as hereinbefore defined and the preservation solution comprises additional components for continued functioning or prevention of damage to certain cellular or organ functions specific to the cell, tissue or organ in question.

In a further aspect of the invention there is provided a method for flushing, preserving or flush preservation of cells, in particular living cells, tissues or organs whereby the cells, tissue or organs are brought into contact with a solution as hereinbefore defined. The method may be for simple hypothermic storage, whereby the cells, tissue or organ are flushed with solution, removed from the normal locus, cooled preferably to temperatures normally in the range between zero and 4° C. and stored. We have found that cells, tissues or organs can be stored for extended periods exceeding those currently practised, for example, heart has been stored for periods of the order of 6-12 hours, and kidney and liver for periods of the order of 48 hours or more. Additionally or alternatively the method is for the preservation of cells, particularly tissue or organs, whereby the cells, tissue or organs have been flushed and brought into a hypothermic state and are contacted with the preservation solution by immersion or perfusion.

Preferably the method of the invention comprises administering to the cells, tissue, organ or to a patient a biologically effective amount of the solution of the invention, at an effective rate or in an effective concentration to maintain or enhance function thereof. Preferably the method is a method for preserving certain cell, tissue or organ function, for example cell metabolism, and/or for temporarily arresting certain functions, for example muscular activity, breakdown or excretion of essential cell components and the like, and/or excretory products for example in the form of bile or urine and the like.

Ischaemia is the situation that results from the stopping of blood flow through an organ. The effects are due to lack of oxygen and nutrients, and accumulation of carbon dioxide and other waste products. It is more damaging at body temperature than in the cold which is why transplant organs are flushed and cooled. Organ donors have frequently suffered trauma and the donor organ may therefore have been subjected to a period of warm ischaemia as a result of the trauma. Adding a period of warm ischaemia experimentally prior to flush copies this situation. It is an advantage that our solution provides protection from such warm ischaemia.

Preferably flush perfusion is carried out at a pressure of up to 300 mmHg, more preferably in the range atmospheric to 200 mmHg, more preferably in the range up to 160 mmHg, more preferably up to 100 mmHg, most preferably up to 50 mmHg.

In a further aspect of the invention there is provided a kit of parts comprising a flush preservation solution having components (i)-(iv) as hereinbefore defined, together with individual components selected from one or more of (v)-(xvii) as hereinbefore defined, for use in the preparation of one or more flush solutions for specific purpose, and serving as a universal flush, preservation or flush preservation solution.

The invention is now illustrated in non-limiting manner with reference to the examples.

EXAMPLE 1

Flush Preservation Solutions Used in the Invention & as Comparison

The preservation solutions involved in this study are shown in the Tables 1 2 and 3, amounts are given in mmol/L. SOLS were made up from a flask half filled with water, to which any or all of lactobionate, KOH, sodium phosphate, glutamine, sucrose, aspirin, allopurinol and nicardipine were added in sequence and dissolved. The colloid (PEG) was then added and the solution made nearly up to volume. NaOH was added to set the pH. The solution was then made up to volume. All solutions were sterilized by filtration and stored in glass bottles at 4° C. and used within 3 days of preparation. Reduced glutathione was added during preparation or immediately before use.

Comparative

UW is a standard original commercial solution (viaSpan/BELZER UW, DU PONT PHARMA). PBS140 (not shown) is composed of phosphate and sucrose (140 mmol/L).

Chemicals

Lactobionic acid (Sigma, L-2398), Allopurinol (Sigma. A-8003), Glutamine (Sigma, G-7029), Reduced Glutathione (Sigma, G-4251), Aspirin (Sigmam. A-5376), Diltiazem (Sigma. D-2521), Taurocholic Acids (Sigma, T-4009), Polyethylene Glycol (Sigma, P-2263), Nicardipine (Sigma, N-7510), Adenosine (Sigma. A-9251), Glycine (Sigma, G07126), N-Acetyl-Cysteine (Sigma, A-8199), Albumin, Bovine (Sigma, A-7906), Alanine (Sigma, A-5824), Glucose (BDH, 10117 Y), Gelofusine (B. Braun Medical Ltd., Lot: 8274D14 F), KOH (BDH, 102104V), NaOH (BDH, 102524x), $Na_2HPO_4$ (BDH, 102494C), $NaH_2PO_4$ $2H_2O$ (BDH, 310324Q), Sucrose (BDH, 102745C), $MgCl_2$ $6H_2O$ (BDH, 101494 V).

TABLE 1

Composition of Commercially Available Preservation Solutions
University of Wisconsin Solution

| Contents in mmol/l | |
|---|---|
| $KHPO_4$ | 25 |
| KCl | 5 |
| Adenosine | 5 |
| Glutathione | 3 |
| $MgSO_4$ | 5 |
| Raffinose | 30 |
| Allopurinol | 0.01 |
| K-Lactobionate | 100 |
| Pentastarch | 5 |
| Osmolality | 320 mosmol/L |
| PH | 7.4 |

TABLE 2

Composition of the cold preservation solutions of the invention used in the study

| | Mmol/L | | | | | | |
|---|---|---|---|---|---|---|---|
| | SOL 4 | SOL 5 | SOL 6 | SOL 7 | SOL 8 | SOL 12 | SOL 13 |
| Lactobionate | 50 | 50 | 50 | | | 50 | 50 |
| KOH | 5 | 5 | 5 | 5 | 5 | 5 | 5 |
| NaOH | 40 | 40 | 40 | 5 | 5 | 55 | 40 |
| Glutathione | 3 | 3 | 3 | 3 | 3 | 3 | 3 |
| $Na_2HPO_4$ | 26.45 | 26.45 | 26.45 | 26.45 | 26.45 | 26.45 | 26.45 |
| Glutamine | 20 | 20 | 20 | 20 | 20 | 20 | 20 |
| $NaH_2PO_4 2H_2O$ | 16.66 | 16.66 | 16.66 | 16.66 | 16.66 | 16.66 | 16.66 |
| Sucrose | 100 | 100 | 100 | 100 | 100 | 100 | 100 |
| Aspirin | 0.5549 | 0.5549 | 0.5549 | 0.5549 | 0.5549 | 0.5549 | 0.5549 |
| Allopurinol | 0.3673 | 0.3673 | 0.3673 | 0.3673 | 0.3673 | 0.3673 | 0.3673 |
| Diltiazem | 0.0221 | 0.0221 | 0.0221 | 0.0221 | 0.0221 | | 0.0221 |
| Adenosine | | | | | | | 5 |
| Gelofusine (ml/L) | | 100 | 300 | 100 | 300 | | |
| Nicardipine | | | | | | 0.005 | |
| Osmolality | 300 | 320 | 350 | 280 | 300 | 300 | 300 |
| pH | 7.0 | 7.0 | 7.0 | 7.0 | 7.0 | 7.0 | 7.0 |

TABLE 3

Composition of the cold preservation solutions of the invention (cont).

| | Mmol | | | | | | | | |
|---|---|---|---|---|---|---|---|---|---|
| | Sol 14 | Sol 15 | Sol 16* | Sol 17# | Sol 18# | Sol 19# | Sol 20# | PBSL | PBSH |
| Lactobionate | 50 | 50 | 50 | 50 | 50 | | 50 | 50 | |
| KOH | 5 | 5 | 5 | 5 | 5 | 5 | 5 | 16 | |
| NaOH | 60 | 50 | 50 | 50 | 45 | | 45 | 35 | |
| Glutathione | | 3 | 3 | 3 | 3 | 3 | 3 | 3 | |
| $Na_2HPO_4$ | 26.45 | 26.45 | 26.45 | 26.45 | 26.45 | 26.45 | 26.45 | 26.45 | 42.3 |
| Glutamine | 20 | 20 | 20 | 20 | 20 | 20 | 20 | 20 | |
| $NaH_2PO_4$ $2H_2O$ | 16.66 | 16.66 | 16.66 | 16.66 | 16.66 | 16.66 | 16.66 | 16.66 | 10.67 |
| $KH_2PO_4$ | | | | | | | | | 16 |
| Sucrose | 100 | 100 | 100 | 100 | 100 | 100 | 100 | 100 | 100 |
| Aspirin | 0.5549 | 0.5549 | 0.5549 | 0.5549 | 0.5549 | 0.5549 | 0.5549 | 0.5 | |
| Allopurinol | 0.3673 | 0.3673 | 0.3673 | 0.3673 | 0.3673 | 0.3673 | 0.3673 | 0.4 | |
| Diltiazem | 0.0221 | 0.0221 | 0.0221 | 0.0221 | 0.0221 | 0.0221 | | | 0.5 |
| Nicardipine | | | | | | | 0.005 | 0.005 | |
| Adenosine | | | | | | | | | |
| Glycine | 10 | | | | | | | | |
| N-Acetyl-Cysteine | 10 | | | | | | | | |
| NaCl | | | | | | | | | 12 |
| $MgCl_2 6H_2O$ | | 5 | | | | | | | 5 |
| $CaCl_2 2H_2 0$ | | | | | | | | | 0.6 |
| Polyethylene Glycol | | | 0.133 | 0.133 | 1.33 | 1.33 | 1.33 | 1.0 | |
| Osmolality | 300 | 30 | 320 | 340 | 380 | 290 | 380 | 380 | |
| pH | 7.0 | 7.0 | 7.0 | 7.0 | 7.0 | 7.0 | 7.0 | 7.0 | |

Molecular weight of polyethylene Glycol * 8000 dalton # 20000 dalton

SOL 4, SOL 5, SOL 6, SOL 7, SOL 8, S0L 12, SOL 13, SOL 14, SOL 15, SOL 16, SOL 17, SOL 18, SOL 19, SOL 20 were all based on SOL 4 but with different additives. The effects of individual additives were studied, and the more significant are mentioned as follows. Specific results are given below in respect of SOL 20.

When glutathione was replaced with glycine and n-acetyl-cysteine an advantage was seen in 24 hour cold rat liver preservation, as evidence by greater bile production than in SOL 4 group during the reperfusion. When nicardipine was added in place of diltiazem in SOL 4, the new solution was found to be more effective than SOL 4 in 24 hour cold rat liver preservation, as indicated by greater bile production and less enzyme release than that for the SOL 4 group during the reperfusion. In a comparison of different PEGs, PEG 20K appears slightly more effective than PEG 8K, as evidenced by numerically less AST and LDH release during the reperfusion. The concentration of PEG 20K in SOL 17 was raised from 0.133 mmol/L to 1.33 mmol/L to yield SOL 18 which was found to be more effective in 24 hour rat liver cold preservation than SOL 17, SOL 4 and UW solution, as indicated by greater bile production and less enzyme release and higher bile acid extraction. The final solution SOL 20 was more effective than SOL 4 or UW solution in 24 hour and 48 hour rat liver cold preservation, as evidenced by greater bile production and less enzyme release and higher bile acid extraction. SOL 20 has advantages for protection of the rat liver from ischemia damage.

Liver Preservation: Materials and Methods

1. Isolated Perfused Rat Livers (IPRL)

The method for this model described by Gores and colleagues (Gores et al, 1986) was adopted and modified for this study. Inbred male Wistar rats weighing 230-280 gram were obtained from the Biomedical Service of the University of Leeds.

1.1 Donor Liver Harvesting

The rat was anesthetized by intraperitoneal injection of pentobarbital (60 mg/kg) without prior fasting. The abdomen was opened through a long midline incision. The liver was checked to be without tumor or any evidence of inflammation. The common bile duct was located, cut in its anterior wall and cannulated with a polyethylene catheter of 1 mm in diameter which was secured in place by a silk ligature, the bile duct was then divided distally. 0.5 ml of normal saline solution containing 500 units of heparin was injected via the penile vein. The abdominal aorta was isolated and cannulated with a 2 mm diameter polyethylene catheter, through which the liver was flushed in situ with 30 ml of one of the ice-cold experimental preservation solutions. In the meantime, the thoracic cavity was opened, the thoracic aorta was clamped, and the inferior vana cava (IVC) was cut open to allow the perfusate to escape. Ice-cold normal saline was put around the liver to cool it. Another 2 mm diameter polyethylene catheter was inserted into the portal vein and secured by a silk ligature, 15 ml of the same preservation solution was perfused through the liver via this catheter. The donor liver was then removed and stored at 4° C. for 24-48 hours in the same preservation solution. In the pre-flush warm ischaemia group, the rat heart was stopped before the livers were flushed in situ with the PBS140 or UW solution. In the pre-reperfusion warm ischaemia group, 30 minutes warm ischemia in a chamber of 37° C. was imposed just before the reperfusion.

1.2 Reperfusion of Stored Livers.

The basic solution for the isolated liver reperfusion in the present study was physiological saline (Table 4).

TABLE 4

The Composition of Physiological Saline.

| Components | mM/L |
|---|---|
| NaCl | 114.0 |
| $K_2HPO_4·3H_2O$ | 2.5 |
| $MgCl_2·6H_2O$ | 1.2 |
| Na-Lactate ($C_3H_5O_3Na$) | 4.0 |
| $NaHCO_3$ | 25.0 |
| $CaCl_2·2H_2O$ | 2.0 |

TABLE 4-continued

The Composition of Physiological Saline.

| Components | mM/L |
|---|---|
| L-Alanine | 6.0 |
| Osmolality (mOsm/L) | 297 |
| PH | 7.0 |

Washed bovine red blood cells were added to increase the oxygen capacity. 2% of the bovine serum albumin (fraction 5, Sigma) was added to maintain the oncotic pressure. The composition of the perfusate is outlined in Table 5.

TABLE 5

The composition of the perfusate

| Composition | volume |
|---|---|
| Physiological Saline | 160 ml |
| Fresh Bovine Red Blood Cells | 80 ml |
| Bovine Serum Albumin | 5 g (=2% in solution) |
| Taurocholic Acid | 60-80 mg (about 50 um/hr) |

Fresh bovine blood was obtained from the abattoir. The blood was centrifuged for 10 minutes at 3000 rpm, the red blood cell were separated and washed with normal saline twice and then decanted into the final perfusate. The haematocrit of the perfusate was around 30-35%. The pH was measured and titrated to 7.4 by the addition of 8.4% sodium bicarbonate, this usually needed 4.0 ml.

1.3 Apparatus.

The perfusion apparatus consisted of a perspex cabinet in which the temperature was maintained at 37° C. by two fan heaters, a roller pump (Watson-Marlow Co.), a membrane oxygenator (COBE*), two syringe pumps, a magnetic stirrer and a perfusion circuit connecting the liver (in a perspex container) via the portal vein cannulation at one end to a glass reservoir at the other. All components were inside the cabinet except for the pump. The roller pump drove the circulation, two syringe pumps were for the separate injection of taurocholic acid and sodium bicarbonate (FIG. 1a).

1.4 Reperfusion

The perfusion circuit including the oxygenator was filled in advance with the perfusate which had been oxygenated with a 95%/5% $O_2/CO_2$ mixture at a flow rate of 100-200 ml/min. Following cold storage, the livers were transferred to the liver container, placed in the perspex cabinet and the portal cannula connected to the inflow tubing. Extreme care was taken to ensure that no air bubbles entered the cannula, in order to avoid embolism to the liver. Both the circulation pump and the syringe pump for the taurocholic acid were started simultaneously. Taurocholate (sodium salt, Sigma) was pumped into the perfusion solution at a rate of 60-80 µmol/hr. 8.4% of sodium bicarbonate solution was added into the reservoir as required to maintain the pH of perfusate to about 7.4±0.1, which was measured by blood gas analyser (CIBA-CORNING). The reperfusion flow rate was 15 ml/min. Bile volume was recorded in consecutive 15 minute periods. Samples were obtained from inflow (portal vein), and outflow (hepatic vein) at each 30-minute intervals for the measurement of pH, $pO_2$ and $pCO_2$, and the samples from the hepatic vein were also used for the determination of lactate dehydrogenase (LDH), aspartate aminotransferase (AST) and alanine aminotransferase (ALT). At the end of reperfusion, samples from the perfusate were taken for the measurement of taurocholic acid concentration to calculate the bile acid extraction percentage. The bile was collected, recorded and analysed for its concentration of bile acids at the end of the 2-hour of reperfusion. The bile volume was expressed as µl. (g liver)$^{-1}$. (15 min.)$^{-}$ or µl. (g liver)$^{-1}$. (2 hr)$^{-1}$. Liver weights were recorded before and after storage to yield the net liver weight and the liver weight change. The liver weight was also recorded at the end of the reperfusion period to calculate the change in weight.

1.5. Presentation of Results

In order to facilitate both presentation of statistical analysis and also visualization of results observations are presented in both table and graphical form in most instances.

1.6. Statistical Analysis

Data are expressed as mean±SEM throughout. In each experimental group, the animal number is 6 (n=6) unless otherwise stated. The statistical tests used in this thesis are Students 't' test or one way analysis of variance with Dunnets test for multiple comparison with a control, or Tukey test for multiple comparisons. Significance was assumed at P<0.05.

SOL 20 was developed from results obtained with SOL4-19. The results compare the effect of the new solution with solution 4 and UW solution at 24 hours cold rat liver preservation.

1.5.1 Bile Flow.

Figure 2:
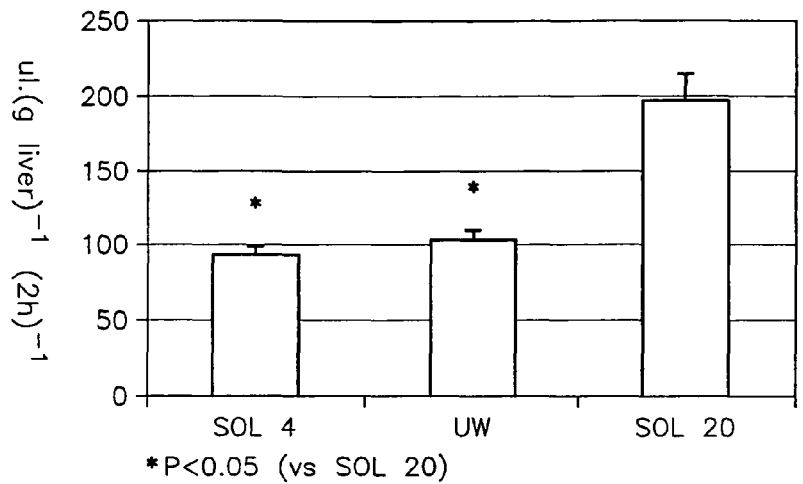
FIG. 2: A graph showing the cumulative results of bile flow rates in consecutive 15 minute intervals during the reperfusion for the SOL 4, UW, and SOL 20 groups.

In these three groups, the bile production in SOL 20 was the best seen in this model. Bile flow commenced within 5 minutes of the livers being placed in the circuit and continued throughout the whole 2 hours of the reperfusion period. The appearance of the bile in each group was excellent: the colour was deeply yellow, and very clear. The bile flow rates per gram of liver for the 2 hours were: 93.4±5.3, 103.4±6.7 and 198.3±18.0 µl for the SOL 4, UW and SOL 20 groups respectively. The best result was with SOL 20, with significant differences compared either with SOL 4 or with UW groups. The results of bile flow rates [µl. (g liver)$^{-1}$. (15 min)$^{-1}$] in consecutive 15 minute periods during the reperfusion for the SOL 4, UW and SOL 20 groups are displayed in Table 6 and cumulative results in FIG. 2.

TABLE 6

Bile flow rates [µl. (g liver)$^{-1}$ · (15 min)$^{-1}$] in consecutive 15 minute periods during the reperfusion for the SOL 4, UW and SOL 20 groups following 24-hour cold preservation.

| | Time (min.) | | | | | | | |
|---|---|---|---|---|---|---|---|---|
| | 0-15 | 15-30 | 30-45 | 45-60 | 60-75 | 75-90 | 90-105 | 105-120 |
| SOL 4 | 5.72 ± 1.3 | 10.14 ± 1.6* | 10.72 ± 0.98* | 14.45 ± 1.3* | 13.09 ± 1.0* | 14.45 ± 2.1* | 11.38 ± 0.87* | 11.09 ± 0.62* |
| UW | 4.99 ± 0.99 | 9.72 ± 1.3* | 14.01 ± 2.2* | 19.01 ± 1.7* | 16.90 ± 1.2* | 16.96 ± 1.4* | 11.92 ± 0.63* | 9.78 ± 1.1* |
| SOL 20 | 9.94 ± 2.3 | 19.42 ± 3.4 | 24.10 ± 4.4 | 35.15 ± 3.3 | 28.33 ± 3.8 | 30.76 ± 1.9 | 26.84 ± 2.4 | 23.78 ± 2.3 |

*P < 0.05 (vs SOL 20)

1.5.2. Enzyme Release.

1.5.2.1 ALT release: During the reperfusion period, livers stored in SOL 20 group for 24-hour released significantly less ALT (U/L) than that for the UW or SOL 4 groups (Table 7), otherwise the ALT released from the livers stored in the UW were no difference compared from that in SOL 4.

TABLE 7

ALT (U/L) release during the reperfusion for the SOL 4, UW and SOL 20 groups following 24-hour cold preservation.

| | Time (min.) | | | | |
|---|---|---|---|---|---|
| | Rinse | 30 | 60 | 90 | 120 |
| SOL 4 | 64.8 ± 6.8 | 30.3 ± 4.3* | 32.0 ± 2.9* | 44.9 ± 3.2* | 80.7 ± 8.1* |
| UW | 74.5 ± 9.8* | 24.8 ± 2.9 | 37.6 ± 3.7* | 50.3 ± 3.5* | 73.0 ± 6.7* |
| SOL 20 | 38.6 ± 2.9 | 16.2 ± 1.1 | 20.6 ± 1.2 | 28.6 ± 2.2 | 35.4 ± 1.7 |

*P < 0.05 (vs SOL 20)

1.5.2.2 AST release: The AST (U/L) released from the livers stored in the SOL 20 were less than that either in the UW or SOL 4, with significant differences at the Rinse and the 30, 120 minute points compared with the UW group and at the 30, 90, 120 minute points compared with the SOL 4 group during the reperfusion (Table 8). There were no differences between the SOL 4 and UW groups.

TABLE 8

AST (U/L) release during the reperfusion for the SOL 4, UW and SOL 20 groups following 24-hour cold preservation.

| | Time (min.) | | | | |
|---|---|---|---|---|---|
| | Rinse | 30 | 60 | 90 | 120 |
| SOL 4 | 38.7 ± 6.8 | 25.2 ± 3.0* | 32.9 ± 6.2 | 49.0 ± 8.0* | 86.6 ± 14* |
| UW | 55.3 ± 6.4* | 23.8 ± 2.0* | 33.6 ± 1.8 | 46.2 ± 2.7 | 69.2 ± 3.6* |
| SOL 20 | 27.9 ± 1.3 | 13.3 ± 0.92 | 21.6 ± 1.2 | 26.6 ± 1.4 | 30.2 ± 1.5 |

*P < 0.05 (vs SOL 20)

1.5.2.3 LDH release: The livers stored in the SOL 20 group for 24-hour released significantly less LDH (U/L) than that either in the UW or SOL 4 groups (Table 9). Compared with the UW group, whilst the livers stored in the SOL 4 also released less LDH, the difference was not statistically significant.

TABLE 9

LDH (U/L) release during the reperfusion for the SOL 4, UW and SOL 20 groups following 24-hour cold preservation

| | Time (min.) | | | | |
|---|---|---|---|---|---|
| | Rinse | 30 | 60 | 90 | 120 |
| SOL 4 | 544 ± 36* | 204 ± 20* | 241 ± 31* | 317 ± 57* | 461 ± 52* |
| UW | 565 ± 56* | 183 ± 18* | 216 ± 18* | 295 ± 24* | 390 ± 21* |
| SOL 20 | 358 ± 12 | 92 ± 18 | 106 ± 16 | 130 ± 16 | 172 ± 25 |

*P < 0.05 (vs SOL 20)

Figure 3:
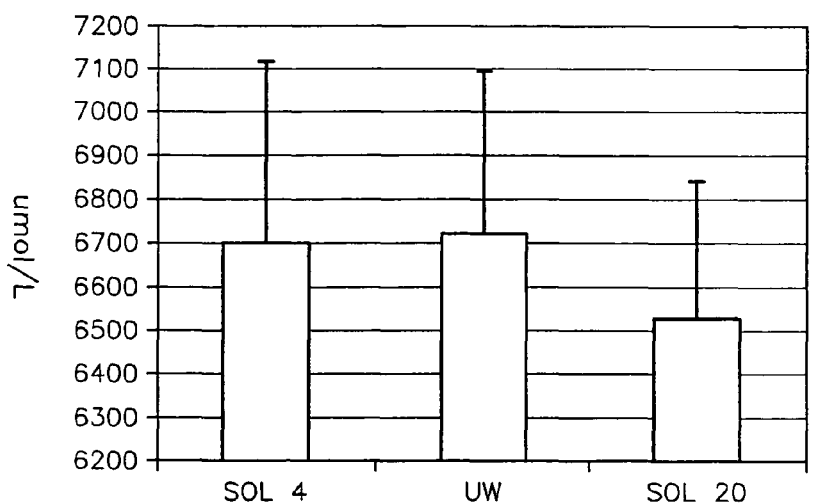
FIG. 3: A graph showing the bile acid concentration in bile during the reperfusion for the SOL 4, UW, and SOL 20 groups.
Figure 4:
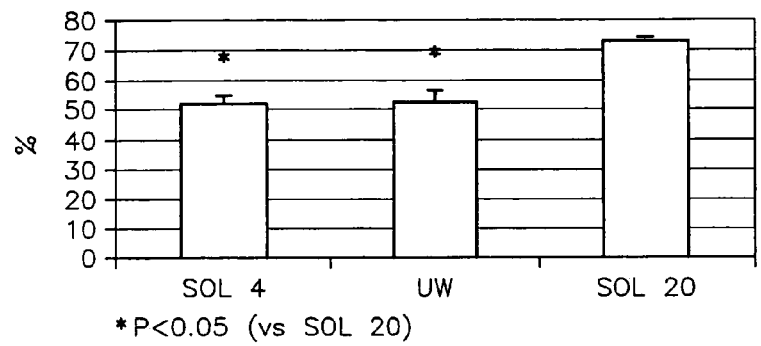
FIG. 4: A graph showing the bile acid extractions during the reperfusion for the SOL 4, UW, and SOL 20 groups.

1.5.3. The bile acid concentrations in bile during the reperfusion for the SOL 4, UW and SOL 20 groups were 6700±417, 6725±371 and 6529±317 µmol/L respectively, there was no significant differences between these groups (FIG. 3). The bile acid extraction (%) during the reperfusion for the SOL 20 group was higher than that for the SOL 4 or UW groups (FIG. 4). Compared with the UW group, the bile acid extraction for the SOL 4 group was not significantly different.

1.5.4. The weight of all the livers stored in SOL 4, UW or SOL 20 decreased after 24-hour cold preservation. There was a significant difference between SOL 4 and UW or SOL 20 groups (Table 10). The liver weights for the SOL 20 group was also decreased after the 2 hours of reperfusion, in the other two groups, the liver weights were increased after the reperfusion, there were significant differences between SOL 20 and SOL 4 or UW.

TABLE 10

Liver weights change (%) after 24-hour cold preservation and after 2-hour reperfusion for the SOL 4, UW and SOL 20 groups.

| | After Preservation | After Reperfusion |
|---|---|---|
| SOL 4 | −0.78 ± 0.82 | 3.97 ± 1.0* |
| UW | −2.39 ± 0.62** | 5.27 ± 1.1* |
| SOL 20 | −2.13 ± 0.72** | −0.18 ± 1.8 |

*P < 0.05 (vs SOL 20);
**P < 0.05 (vs SOL 4)

Figure 5:
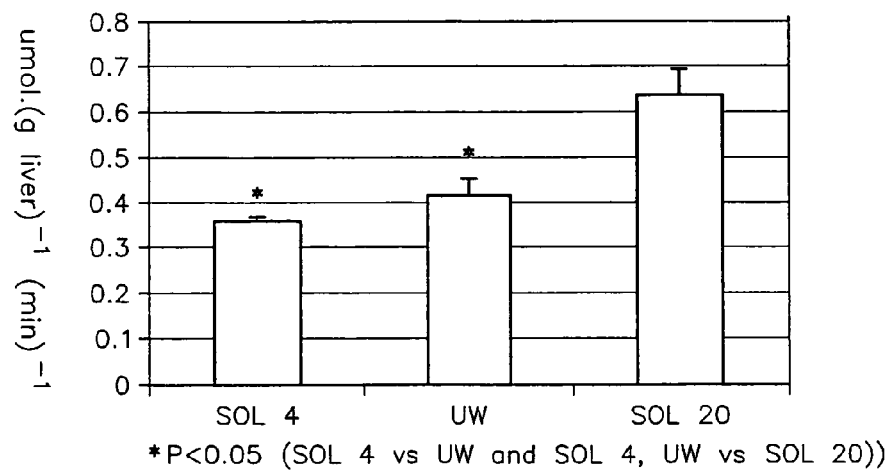
FIG. 5: A graph oxygen consumption of livers stored in SOL 4, UW, and SOL 20 during reperfusion.

1.5.5. The oxygen consumptions of the livers stored in SOL 4, UW and SOL 20 during the reperfusion period were: 0.360±0.007, 0.417±0.016 and 0.646±0.04 µmol. (g liver)$^{-1}$. (min)$^{-1}$ respectively, there were significant differences for the SOL 20 group compared with the SOL 4 or UW groups, also significant difference between the UW and SOL 4 groups (FIG. 5).

Figure 6:
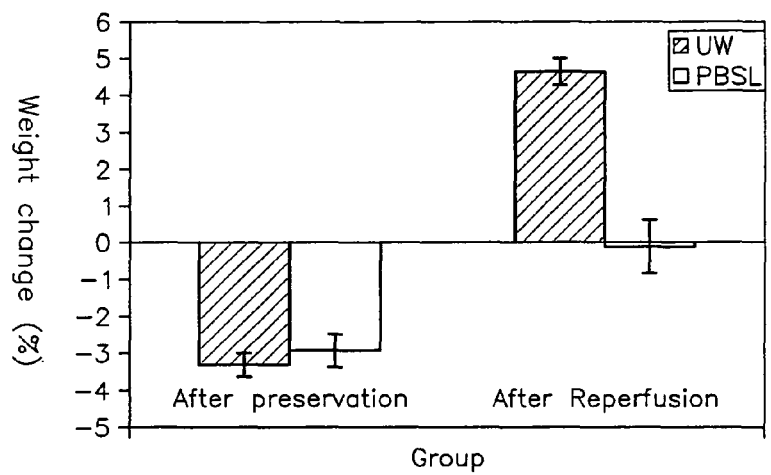
FIG. 6: A chart comparing the liver weight change after 24 hours of cold preservation and after 2 hours of reperfusion using UW or PBSL solution.
Figure 7:
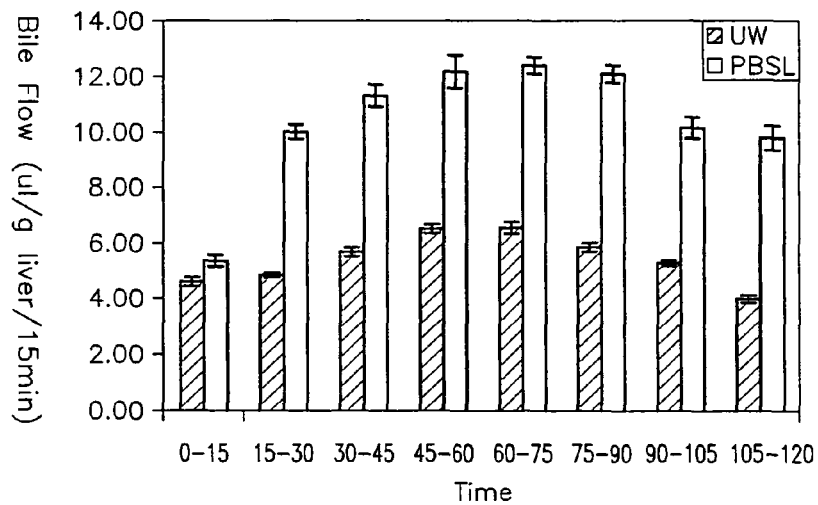
FIG. 7: A chart comparing bile flow in consecutive 15 minute periods after 24 hours of cold preservation using UW or PBSL solution.
Figure 8:
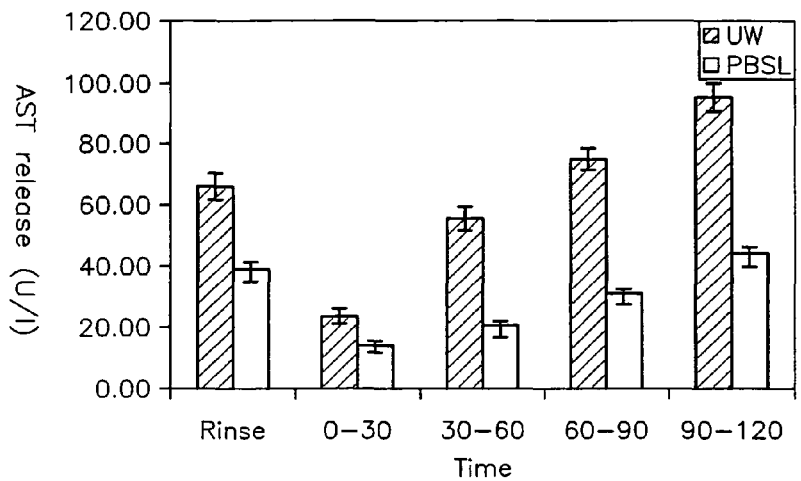
FIG. 8: A chart comparing AST release after 24 hours of cold preservation using UW or PBSL solution.
Figure 9:
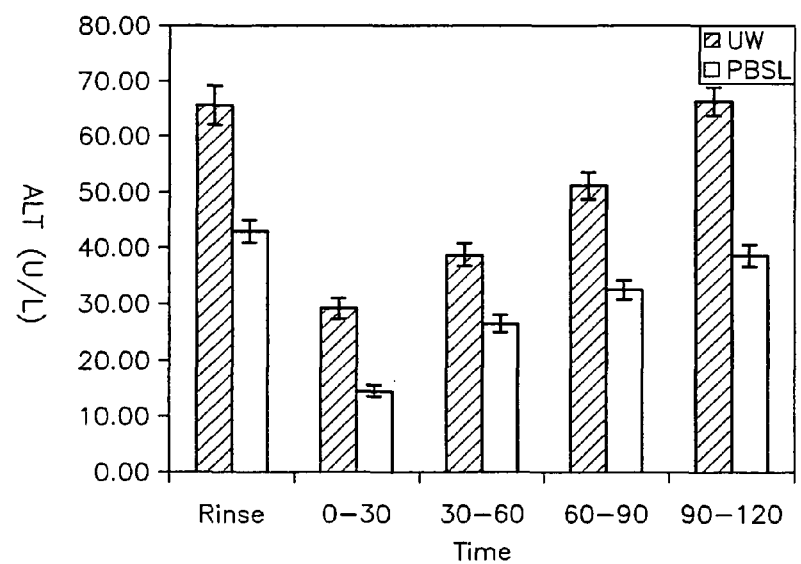
FIG. 9: A chart comparing ALT after 24 hours of cold preservation using UW or PBSL solution.

A completely independent further set of observations was made on PBSH, the results are shown in FIGS. 6-10 inclusive. These results confirm that PBSL causes less swelling of the liver than UW (FIG. 6). Bile flow after preservation in PBSL was approaching twice that following preservation in UW (FIG. 7). AST release was lower with PBSL (FIG. 8) as were ALT (FIG. 9) and LDH (FIG. 10). All of these results were highly significant confirming the advantages of PBSL over UW preservation solution.

2. Heart Preservation: Materials and Methods.

Experiments were carried out under a Home Office Licence in compliance with Home Office guidelines for animal care.

2.1 Perfusion Apparatus.

An isolated working rat heart model was used as described by Neely J R (7). This apparatus consisted of the following parts:

1) Langendorff reservoir with water jacket and glass filter at the bottom outlet.

2) Heart Chamber and cannula assembly. A Teflon bung held two stainless steel cannulas grooved to accommodate ligatures. One cannula was straight to fit the aorta and was fitted with four side arm connectors for Langendorf perfusion, cardioplegia perfusion, pressure and heart rate measurement, and for aortic outflow measurement. The other cannula was angular to facilitate cannulation of the left atrium. The perfused heart, supported by the two cannulae fitted loosely into a water jacketed heart chamber.
3. Aortic and atrial bubble traps and compliance chamber.
4. Oxygenation chamber consisting of three water jacketed condenser units with taper connections which provided a large surface area to facilitate oxygenation.
5. Cardioplegia reservoir, situated 60 cm above the heart and through which preservation solution was infused into the heart.
6. Peristaltic pump and filter used to recycle perfusion solution through the oxygenation chamber.
7. Pressure gauge and pen recorder to record heart rate and aortic pressure.

Figure 1B:
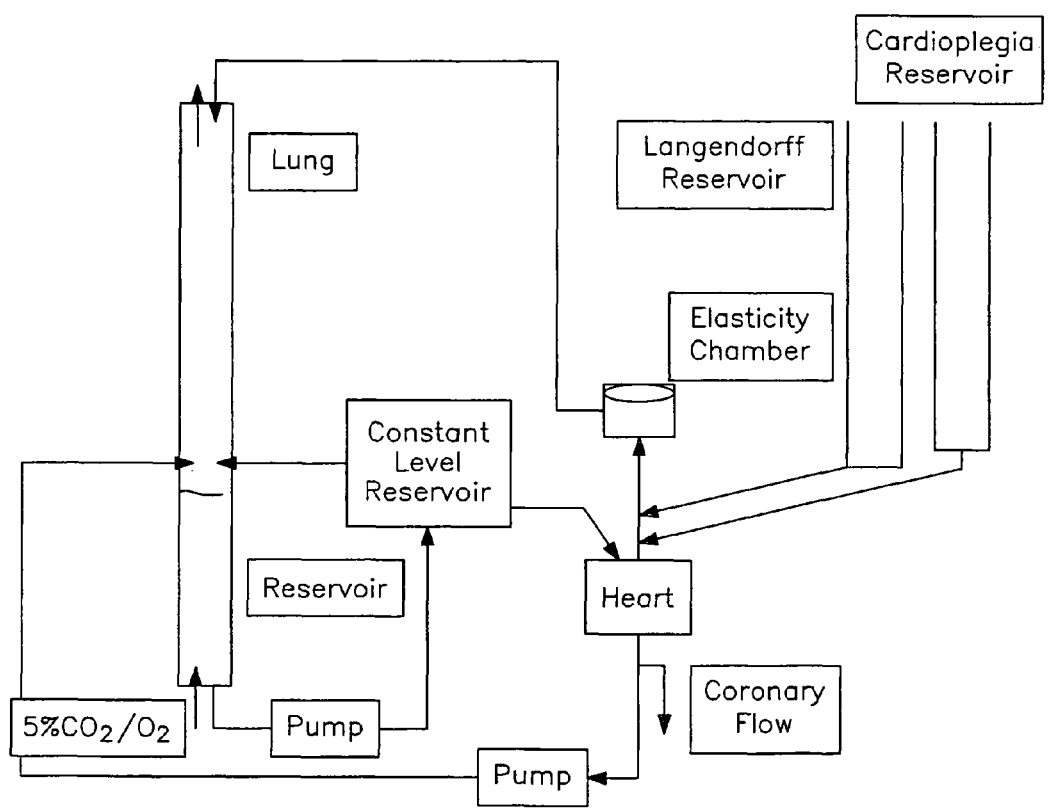
FIG. 1b: A schematic diagram of the heart reperfusion apparatus is shown.

A simplified diagram of the heart reperfusion apparatus is shown in FIG. 1b.

2.2 Perfusion Medium.

The perfusion solution was modified Krebs-henseleit buffer (KHB) equilibriated with 95% oxygen and 5% $CO_2$ at 37° C. The final concentration of salt of this buffer (mmol/l) was NaCl 118, KCl 4.7, $MgSO_4$ 1.2, $CaCl_2$ 2.5, $KH_2PO_4$ 1.2 and $NaHCO_3$ 25.

2.3 Study Protocol.

Male Wistar rats (250-320 g) were anaesthetised with intraperitoneal injection of sodium pentobarbitone (0.26-0.28 ml). Heparin (250 IU) was injected intravenously immediately before surgery. The abdomen was opened to facilitate exposure to the chest, thoracotomy was performed and the heart excised and immediately placed in ice cold saline. Cannulation of the aorta was then carried out and the heart attached to the perfusion apparatus followed by perfusion of KHB solution at 37° C. for an initial wash out and equilibration period during which the heart regained the beating state. During this period the left atrium was cannulated in order to allow the heart to be switched to a pumping mode. In this configuration KHB drains to the left ventricle which in turn pumped the solution to the aorta, from which it passed to the compliance chamber. This chamber was partly filled with air to provide some elasticity to the otherwise rigid system. Pressure development in this chamber forced the solution through a flow meter to a bubble trap situated 100 cm above the heart from which it returned via the oxygenation chamber to be recycled.

Control measurements of cardiac functions included heart rate (HR), systolic pressure (SP), aortic flow (AF), coronary flow (CF) and cardiac output (CO) every five minutes for a duration of 15 minutes. Hearts that achieved aortic flow of less than 45 ml/min, coronary flow of less than 16 ml/min or heart rate of less than 240 beats/min were excluded from the study. The hearts were then flushed with one of the four preservation solutions (25 ml) from the cardioplegia reservoir situated above the heart, and stored for 6 hours at 4° C. The solution tested were St Thomas' Hospital Solution no 2 (STH2), University of Wisconsin Solution, Celsior Solution (CS) and Phosphate Buffered Sucrose Solution (PBSH). The minimum no of hearts included in each group was 6.

After storage for the desired period, reperfusion in a Langendorff mode for a 15 min equilibration period was carried out, followed by conversion to a working heart mode by stopping the Langendorff perfusion and commencing perfusion through the left atrium. The working heart mode lasts for 30 min during which measurement of the cardiac function was made every 5 minutes for comparison to their individual pre-ischaemic control values. Recovery of cardiac functions was expressed as a percentage of the preischaemic control values.

In summary the protocol was as follows:—
Langendorff mode (2-3 min)
Working mode (15 min)
Cardioplegia (25 ml of flush solution).
Preservation (6 hour)
Langendorff reperfusion (15 min)
Working reperfusion (30 min)
Statistical Analysis.

Results in each group were expressed as the mean±SEM. Means of groups were compared using one-way analysis of variance (ANOVA). Statistical significance was accepted at a P value of less than 0.05.

2.4 Results.

TABLE 11

Results (mean ± SEM) for the four experimental groups are shown in the table, expressed as the % recovery of pre-ischaemic function for each of the haemodynamic parameters shown.

| Group | N | HR | SP | AF | CF | CO |
|---|---|---|---|---|---|---|
| STH2 | 8 | 93 ± 2.2 | 80.2 ± 0.8 | 37.5 ± 2.5 | 71.59 ± 5.9 | 47.3 ± 2.1 |
| CS | 8 | 89.6 ± 2.4 | 79 ± 1.2 | 41.5 ± 3.2 | 67.8 ± 4.2 | 47.6 ± 2.0 |
| UW | 7 | 98.7 ± 1.2 | 80.1 ± 1.8 | 47.6 ± 5.0 | 65.3 ± 4.5 | 51.2 ± 4.4 |
| PBSh | 6 | 89.2 ± 2.8 | 90.5 ± 1.5 | 57.1 ± 3.7* | 87.7 ± 5.8* | 66.5 ± 3.3* |

REFERENCES

Andrews P M and Coffey A K (1982). Laboratory Investigation 46, 100-120.
Belzer F O, Ashby B S and Dunphy J E (1967). Lancet 2, 536-539.
Belzer F O and Southard J H (1988). Transplantation 45, 673-676.
Coffey A K and Andrews P M (1983). Transplantation 35, 136-143.
Collins G M, Bravo-Shugarman M and Terasaki P I (1969). Lancet 2, 1219-1222.
Ferwana O, Pirie S C and Potts D J (1988). Clinical Science 74, 261-268.
Ferwana O, Pirie S C and Potts D J (1989). Clinical Science 77, 77-84
Isemer F E, Ludwig A, Schuck O, Bretschneider H J and Peiper H J (1988) Transplantation Proceedings 20, 885-886.
Lam F T, Mayor A, Potts D J and Giles G (1989). Transplantation 47, 767-771.
Ross H, Marshall V C and Escott M O (1976). Transplantation 21, 498-501.
Pirie S C and Potts D J (1986). Clinical Science 70, 443-452

The invention claimed is:

1. A flush preservation solution for liver, kidney and pancreas preservation, which solution comprises:
   i) water for injection; and
   ii) at least one saccharide; and
   iii) at least one component with pH buffer properties;
   iv) at least one component with calcium transport blocking properties or an anti-calcium action activity together with components selected from
   viii) inorganic or organic solutes,
   wherein the flush preservation solution has a pH in the range of 6.8 to 7.0, wherein the flush preservation solution comprises the following combination of component classes given below of the specific type listed:
v) Lactobionic acid;
viii) KOH;
viii) NaOH;
xii) Gluthathione;
iii) Na$_2$HPO$_4$;
iii) NaH$_2$PO$_4$;
xi) Glutamine;
ii) Sucrose;
vi) Aspirin;
xii) Allopurinol;
iv) Nicardipine;
vii) Peg (20,000 MW).

2. A flush preservation solution for liver, kidney and pancreas preservation, which solution comprises:
i) water for injection; and
ii) at least one saccharide; and
iii) at least one component with pH buffer properties;
iv) at least one component with calcium transport blocking properties or an anti-calcium action activity together with components selected from
viii) inorganic or organic solutes,
wherein the flush preservation solution has a pH in the range of 6.8 to 7.0,
and further wherein the flush preservation solution comprises a combination of component classes given below of specific type and substantially in the amount listed when made up to volume in water:

|  | Component Type | Amount mmol/L |
|---|---|---|
| v) | Lactobionic acid | 50 |
| viii) | KOH | 15 |
| viii) | NaOH | 35 |
| xii) | Glutathione | 3 |
| iii) | Na$_2$HPO$_4$ | 26.45 |
| iii) | NaH$_2$PO$_4$ | 16.66 |
| xi) | Glutamine | 20 |
| ii) | Sucrose | 100 |
| vi) | Aspirin | 0.5 |
| xii) | Allopurinol | 0.4 |
| iv) | Nicardipine | 0.005 |
| vii) | Peg (20,000 MW) | 1. |

\* \* \* \* \*